United States Patent [19]
Ralph et al.

[11] Patent Number: 5,752,957
[45] Date of Patent: May 19, 1998

[54] POLYAXIAL MECHANISM FOR USE WITH ORTHOPAEDIC IMPLANT DEVICES

[75] Inventors: James D. Ralph, Oakland; Steven Tatar, Montville, both of N.J.

[73] Assignee: Third Millennium Engineering, LLC, Summit, N.J.

[21] Appl. No.: 799,721

[22] Filed: Feb. 12, 1997

[51] Int. Cl.$^6$ .................................................. A61B 17/70
[52] U.S. Cl. .............................. 606/61; 606/72; 606/73; 606/76
[58] Field of Search .................... 606/61, 60, 72, 606/73, 69, 70, 71, 76, 77, 78; 623/17

[56] References Cited

U.S. PATENT DOCUMENTS

| | | | |
|---|---|---|---|
| 5,476,464 | 12/1995 | Metz-Stravenhagen et al. | 606/61 |
| 5,591,166 | 1/1997 | Bernhardt et al. | 606/61 |
| 5,609,594 | 3/1997 | Errico et al. | 606/61 |
| 5,628,740 | 5/1997 | Mullane | 606/61 |
| 5,662,653 | 9/1997 | Songer et al. | 606/61 |

*Primary Examiner*—Guy V. Tucker
*Attorney, Agent, or Firm*—Joseph P. Errico, Esq.

[57] ABSTRACT

A polyaxial orthopedic device for use with rod implant apparatus includes a hook or a screw having a recess which includes a lower portion and an upper portion, the up per portion is curvate. A rod receiving head having a channel formed therein, and a central bore which is curvately tapered at the inside bottom, and equivalently curvately tapered on the exterior surface, is polyaxially seated in the upper portion of the recess while a post element is inserted down through the head into the lower portion of the recess. The upper portion of the post is widened and curvate so that it seats in the curved lower interior of the bore of the head. The insertion of a rod into the head, onto the top of the post and the subsequent application of a downward force thereon by a nut causes the assembly to lock together, independent of the polyaxial angle of the head to the post and hook, or screw. The post may be held in the recess by means of a transverse dowel positioned in a co-linear transverse hole formed in the recess or post or by sweat locking the post into the recess; the process of sweat locking meaning the insertion of the post into the recess when there is a relative temperature differential being maintained between the two elements such that the post can be inserted into the hole, and the subsequent expansion of the post and contraction of the recess sweat locks the two elements together.

10 Claims, 6 Drawing Sheets

POLYAXIAL MECHANISM FOR USE WITH ORTHOPAEDIC IMPLANT DEVICES

BACKGROUND OF THE INVENTION

1. Field of the Invention

This invention relates generally to a polyaxial mechanism for use with orthopaedic devices, and more particularly to a polyaxial coupling mechanism connecting the top rod coupling portion of an orthopaedic implant device, for example a spinal screw or hook, to the base thereof.

2. Description of the Prior Art

The bones and connective tissue of an adult human spinal column consists of more than 20 discrete bones coupled sequentially to one another by a tri-joint complex which consist of an anterior disc and the two posterior facet joints, the anterior discs of adjacent bones being cushioned by cartilage spacers referred to as intervertebral discs. These more than 20 bones are anatomically categorized as being members of one of four classifications: cervical, thoracic, lumbar, or sacral. The cervical portion of the spine, which comprises the top of the spine, up to the base of the skull, includes the first 7 vertebrae. The intermediate 12 bones are the thoracic vertebrae, and connect to the lower spine comprising the 5 lumbar vertebrae. The base of the spine is the sacral bones (including the coccyx). The component bones of the cervical spine are generally smaller than those of the thoracic and lumbar spine. For the purposes of this disclosure, however, the word spine shall refer only to the cervical region.

Referring now to FIGS. 1, 2, and 3, top, side, and posterior views of a vertebral body, a pair1of adjacent vertebral bodies, and a sequence of vertebral bodies are shown, respectively. The spinal cord is housed in the central canal 10, protected from the posterior side by a shell of bone called the lamina 12. The lamina 12 includes a rearwardly and downwardly extending portion called the spinous process 16, and laterally extending structures which are referred to as the transverse processes 14. The anterior portion of the spine comprises a set of generally cylindrically shaped bones which are stacked one on top of the other. These portions of the vertebrae are referred to as the vertebral bodies 20, and are each separated from the other by the intervertebral discs 22. The pedicles 24 comprise bone bridges which couple the anterior vertebral body 20 to the corresponding lamina 12.

The spinal column of bones is highly complex in that it includes over twenty bones coupled to one another, housing and protecting critical elements of the nervous system having innumerable peripheral nerves and circulatory bodies in close proximity. In spite of these complexities, the spine is a highly flexible structure, capable of a high degree of curvature and twist in nearly every direction. Genetic or developmental irregularities, trauma, chronic stress, tumors, and disease, however, can result in spinal pathologies which either limit this range of motion, or which threaten the critical elements of the nervous system housed within the spinal column. A variety of systems have been disclosed in the art which achieve this immobilization by implanting artificial assemblies in or on the spinal column. These assemblies may be classified as anterior, posterior, or lateral implants. As the classifications suggest, lateral and anterior assemblies are coupled to the anterior portion of the spine, which is the sequence of vertebral bodies. Posterior implants generally comprise pairs of rods, which are aligned along the axis which the bones are to be disposed, and which are then attached to the spinal column by either hooks which couple to the lamina or attach to the transverse processes, or by screws which are inserted through the pedicles.

"Rod assemblies" generally comprise a plurality of such screws which are implanted through the posterior lateral surfaces of the laminae, through the pedicles, and into their respective vertebral bodies, or hooks which hook to the laminae. The screws and hooks are each provided with upper portions which comprise coupling elements, for receiving and securing an elongate rod therethrough. The rod extends along the axis of the spine, coupling to the plurality of screws and/or hooks via their coupling elements. The rigidity of the rod may be utilized to align the spine in conformance with a more desired shape.

It has been identified, however, that a considerable difficulty is associated with inserting screws and hooks along a misaligned curvature and simultaneously exactly positioning the coupling elements such that the rod receiving portions thereof are aligned so that the rod can be passed therethrough without distorting the screws. Attempts at achieving proper alignment with fixed headed screws and hooks is understood to require increased operating time, which is known to enhance many complications associated with surgery. Often surgical efforts with such fixed axes devices cannot be achieved, thereby rendering such instrumentation attempts entirely unsucessful.

The art contains a variety of attempts at providing instrumentation which permit a limited freedom with respect to angulation of the screw and the coupling element. These teachings, however, are generally complex, inadequately reliable, and lack long-term durability. These considerable drawbacks associated with prior art systems also include difficulty properly positioned the rod and coupling elements, and the tedious manipulation of the many small parts in the operative environment.

It is, therefore, the principal object of the present invention to provide a pedicle screw and/or hook having coupling assemblies which provide a polyaxial freedom of implantation angulation with respect to rod reception.

In addition, it is an object of the present invention to provide such an assembly which comprises a reduced number of elements, and which correspondingly provides for expeditious implantation.

Accordingly it is also an object of the present invention to provide an assembly which is reliable, durable, and provides long term fixation support.

Other objects of the present invention not explicitly stated will be set forth and will be more clearly understood in conjunction with the descriptions of the preferred embodiments disclosed hereafter.

SUMMARY OF THE INVENTION

The preceding objects are achieved by the present invention which is a polyaxial rod coupling mechanism having a base member, a post member, a rod receiving member, and a top locking nut. In a first embodiment, there is also a locking pin (or dowel), which pin is not needed in the second embodiment. More particularly, with respect to the first embodiment, the base portion may be either a screw or a hook (or any bone attaching device which requires fixation to a rod ). This base member includes a recess formed in the upper portion thereof and a transverse hole extending through the recess. The upper portion of this recess includes a concave taper such that the upper portion of the recess forms a bowl having a constant radius of curvature. The lower portion of the recess is the portion which includes the transverse hole.

The post member has a lower portion which is formed to seat in the recess of the base member. The lower portion of the post further includes a transverse hole such that when said lower portion is positioned in the recess of the base member, the transverse holes of the base member and the lower portion of the post member are co-linear. The post member is securely retainable in the recess of the base member by means of a locking pin (or dowel) which is insertable into the co-linear transverse hole formed by the above-mentioned transverse holes of the base and post members.

The upper portion of the post member includes a widened annular section. The upper surface of this section may be flat or roughened to provide an enhanced frictional dynamic with a metal rod (such as is to be pressed against it—as set forth more fully hereinbelow). The lower surface of the widened annular section defines a cross-section (taken along the axial length of the post member) which is curvate, and as such forms an arc of a circle (in three dimensions, a section of a sphere).

The rod receiving member is a cylindrical element having a central bore and a channel formed transversely therethrough, said channel dividing the upper portion of the member into two upwardly extending curvate elements. The upwardly extending members are preferably threaded so as to be able to receive a top locking nut of some kind to lock the rod in the channel.

The bottom of the interior bore and the exterior surface of the bottom portion of the rod receiving menber are tapered inwardly with a constant radius of curvature (each preferrably being concentric with the other). The interior bore is sufficiently wide such that the post member may be axially inserted downwardly therethrough until the widened annular section of the post nests in the inwardly tapered bottom surface thereof. The bottom hole in the rod receiving member is therefore smaller in diameter than the widened annular section of the post, however, the lower portion of the post is narrower than the bottom hole, such that the post may freely and polyaxially rotate while the widened annular section is seated in the bottom of the bore. This also permits the lower portion of the post to extend out from the bottom of the bottom of the rod receiving member (and, therefore, be inserted into the recess of the base member).

The upper surface of the post member is of sufficient size top seat above the bottom of the rod receiving channel of the rod receiving member once the post has been fully inserted through the bore. More particularly, with respect to the full assembly of the device, the post portion is inserted down through the bore of the rod receiving member, until the widened annular section thereof seats in the curvate bottom of the bore. The lower portion of the post member is then inserted into the recess of the base until the transverse holes of the post and base members are aligned. A dowel or locking pin is inserted through these co-linearly aligned holes to securely retain the post in the recess. In this position, the bottom exterior of the rod receiving member can float polyaxially between the widened annular section of the post and the curvate upper section of the recess in the base member. The range of angle through which the rod receiving member can polyaxially rotate is determined by the relative geometry of the post and the bore, however, insofar as the diameter of the lower portion of the post is less than the diameter of the hole in the bottom of the bore, the rod receiving member will be able to rotate through angles which are not axially co-linear.

The rod is then placed in the rod receiving channel, and onto the upper surface of the widened annular section of the post. Application of a downward force onto the rod by means of a top locking nut (which is attached to the rod receiving member) causes a relative motion between the rod receiving member and the post such that the lower surface of the widened annular section of the post and the interior curvate surface of the bore of the rod receiving member are compression locked together. This compression lock prevents any further relative motion, thereby stabilizing the implant device sufficiently to provide the immobilization required.

In a second embodiment, the lower portion of the post is rigidly secured in the lower portion of he recess in the base member, not by means of a pin, but rather by "sweat locking" the device together. "Sweat locking", as used herein, shall mean the process by which the lower portion of the post member, which has a diameter which is equal to or greater than the diameter of the lower section of the recess in the base member when each is at the same temperature, is cooled to cause a sufficient reduction in its diameter, and/or the recess is heated to permit thermal expansion of the recess to a diameter which is greater than the lower portion of the post, and the post is driven into the recess prior to thermal equilibration. Subsequent thermal conduction and settling causes the relative expansion of the post in the recess, providing a secure locking of the post in the recess without the need for a dowel.

DETAILED DESCRIPTION OF THE PREFERRED EMBODIMENT

While the present invention will he described more fully hereinafter with reference to the accompanying drawings, in which particular embodiments and methods of implantation are shown, it is to be understood at the outset that persons skilled in the art may modify the invention herein described while achieving the functions and results of this invention. Accordingly, the descriptions which follow are to be understood as illustrative and exemplary of specific structures, aspects and features within the broad scope of the present invention and not as limiting of such broad scope.

Figure 2:
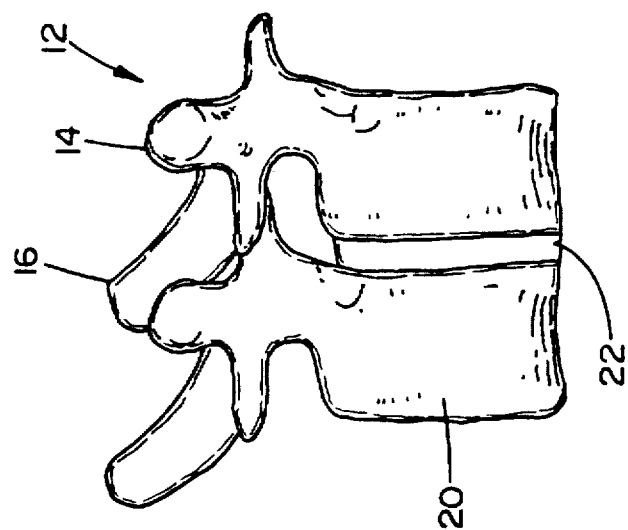
FIG. 2 is a side view of a pair of adjacent vertebrae of the type shown in FIG. 1.
Figure 1:
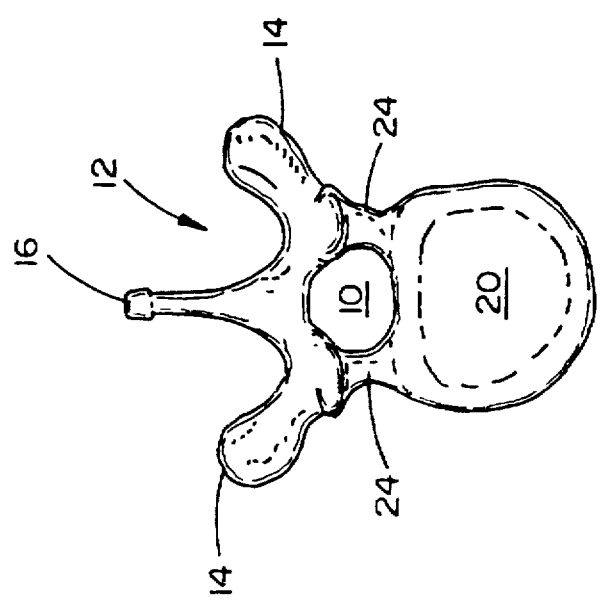
FIG. 1 is a top view of a human vertebra, which is representative of the type for which the present invention is useful for coupling thereto a rod apparatus.
Figure 3:
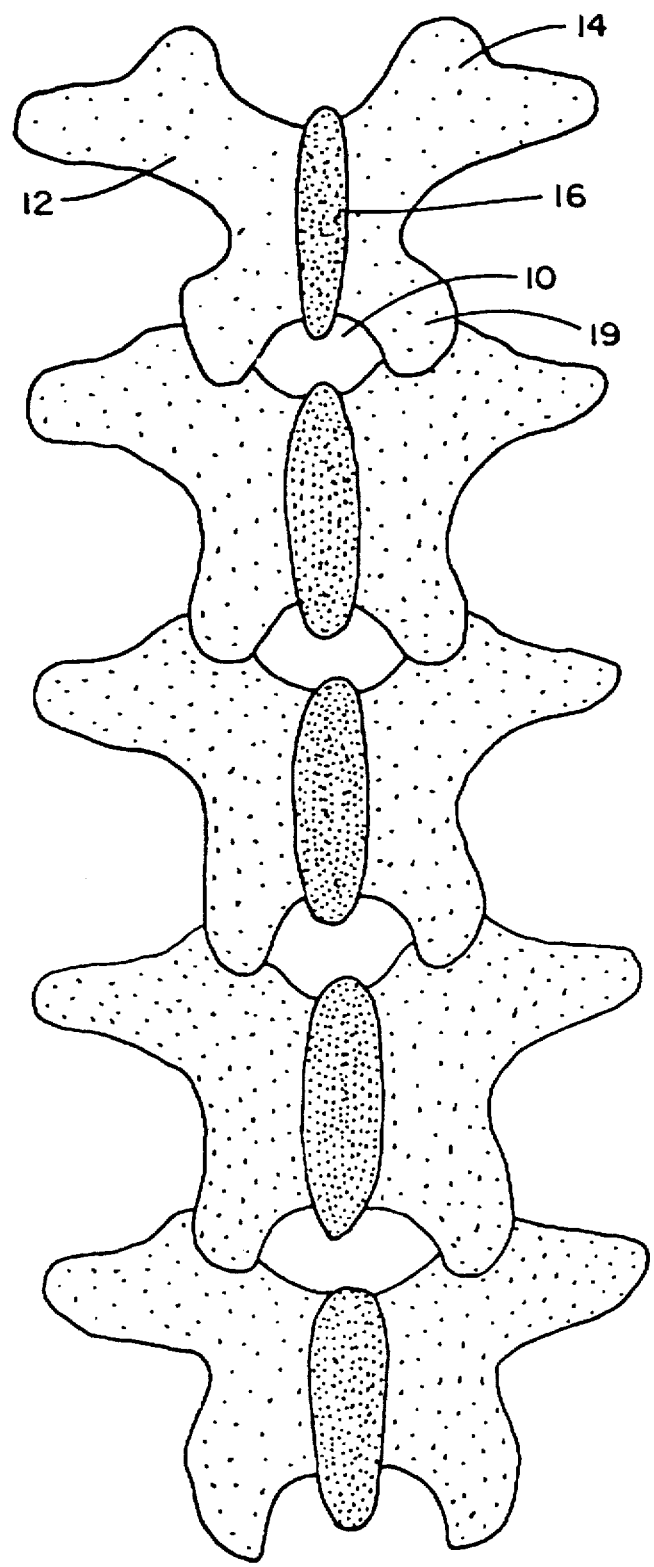
FIG. 3 is a posterior view of a sequence of vertebrae of the type shown in FIGS. 1 and 2.
Figure 4:
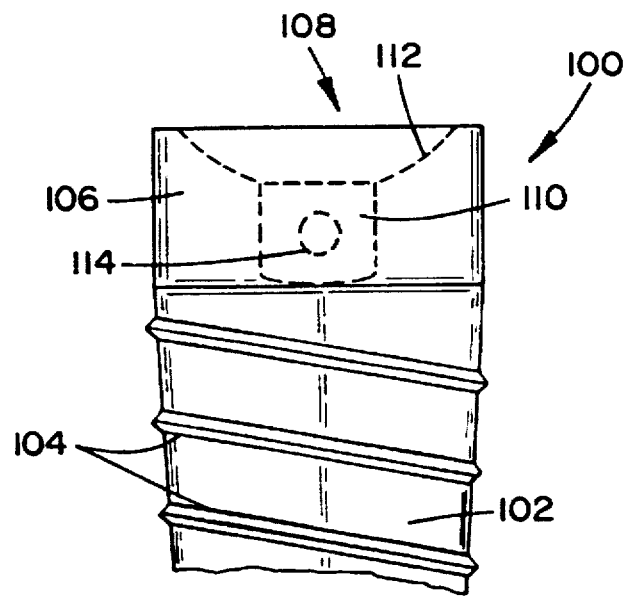
FIG. 4 is a side view of a bone screw which is an aspect of the present invention.

Referring now to FIG. 4, a screw 100 of the present invention is shown in a side view. The screw 100 comprises a standard shaft portion 102 of a bone screw, having a threading 104 provided thereon. The upper portion 106 of the screw 100, however, comprises a recess 108 which is divided into a cylindrical (which may be tapered) lower portion 110, and a curved (preferably with a constant radius of curvature) upper portion 112. The upper portion 106 of the screw, also includes a through hole 114 which extends through the screw transverse to the long axis of the shaft, and through the lower portion 110 of the recess 108 formed in the top thereof.

Figure 5:
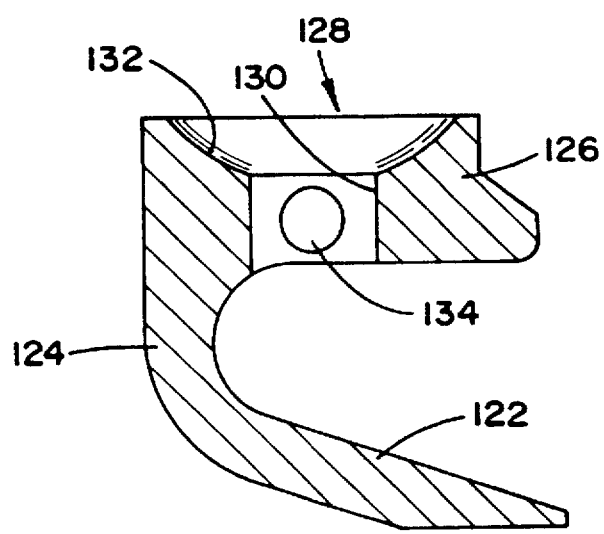
FIG. 5 is a side view of a lamina hook which is an aspect of the present invention.

Referring now to FIG. 5, a lamina hook 120 of the present invention is provided in a side cross-section view. The hook 120 comprises a lower blade portion 122 which is designed to seat under the lamina, a curved portion 124 which is designed to cup the lateral edge of the lamina, and a upper portion 126 which forms a base for the polyaxial head (see FIG. 6). The upper portion 126 of the hook 120 is substantially similar to the upper portion 106 of the screw 100 shown in FIG. 4. The base 106 therefore includes a recess 128 which is divided into a cylindrical (which may be tapered) lower portion 130, and a curved (preferably with a constant radius of curvature) upper portion 132. The upper portion 126 of the hook 120 also includes a through hole 134 which extends through the screw transverse to the long axis of the recess 128, and through the lower portion 130 of the recess 128 formed in the top thereof.

It shall be understood, therefore, that the base implant device, having the recess, may be either a hook or a screw (or any other implant device for which a polyaxial head is desireable).

Figure 6:
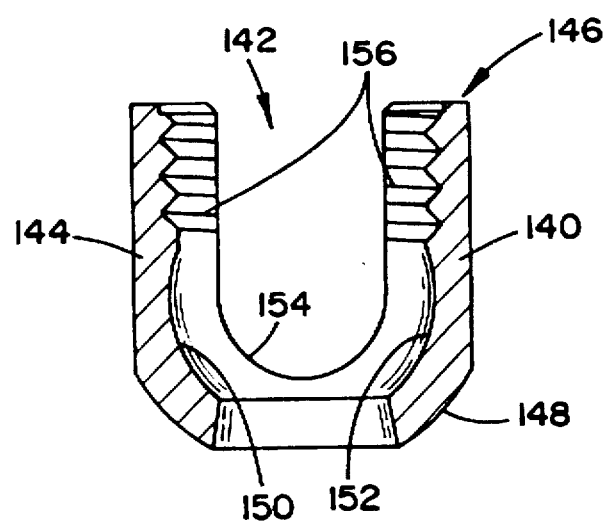
FIG. 6 is a side view of the rod receiving member of present invention.

Referring now to FIG. 6, the rod receiving head 140 of the polyaxial hook is provided in a side cross-section view. The head 140 is a tubular element having a central axial bore 142. The exterior surface 144 of the tube is substantially uniform at the top 146 of the head 140, but inwardly curved at the bottom 148 thereof. The radius of curvature of this bottom exterior surface 148 is preferably constant (spherical) and preferably is equal to the radius of the upper portion 112,132 of the recess 108,128 in the top of the screw 100 or hook 120, respectively.

The interior surface 150 of the head portion 140 has an inwardly curved lower portion 152 which is preferably also curved with a constant radius, and even more preferably substantially concentrically curved with respect to the outer curvature of the lower exterior surface 148.

Figure 10:
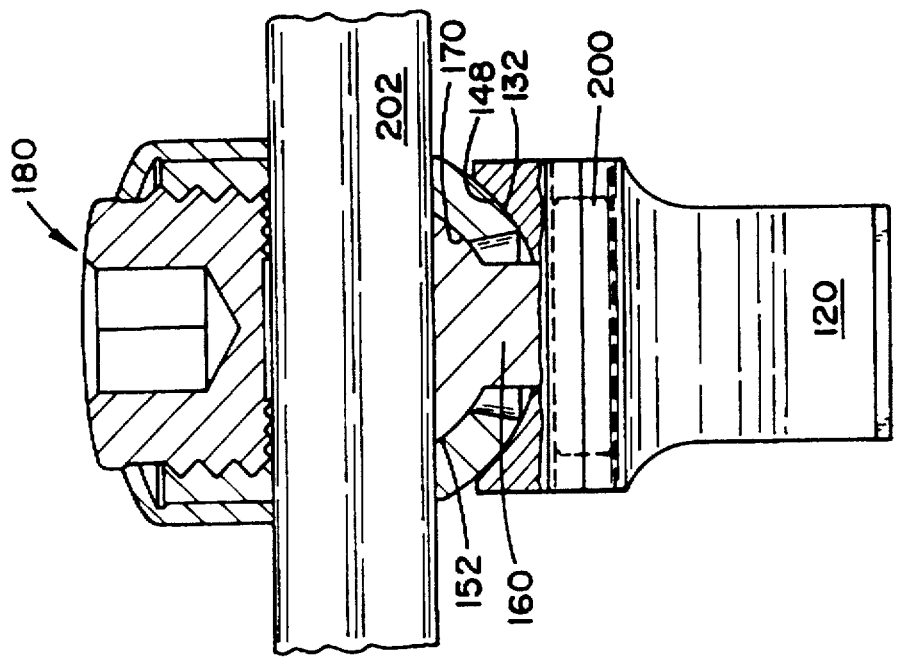
FIG. 10 is a side cross-sectional view of an embodiment of the present invention, a lamina hook embodiment, in its fully assembled disposition having a rod securely locked therein, the plane of the cross-section being perpendicular to the cross-sectional plane of FIG. 9.

The head 140 further comprises a rod receptical defined by a channel groove 154. The depth of the channel groove 154 is determined in proportion to the dimensions of the post element seated therein in a relationship more fully set forth hereinbelow (see FIGS. 9–11, and discussions pertaining thereto). A threading 156 may be provided on the interior (or, not shown, the exterior) surface of the upper portion of the head 140 to receive a locking nut (see FIG. 8).

Figure 7:
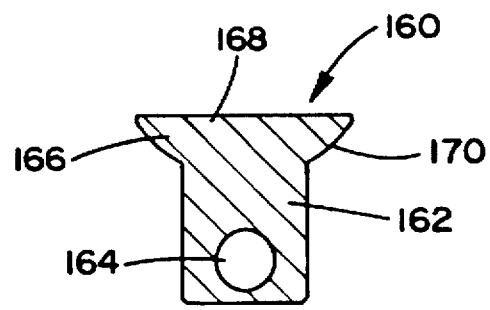
FIG. 7 is a side view of the post member which is an aspect of the present invention.

Referring now to FIG. 7, a post element 160 of the present invention is provided is a side view. The post member 160 has a lower portion 162 which is designed to seat in the lower portion 110,130 of the recess 108,128 of the base member. The lower portion 162 of the post further includes a transverse hole 164 such that when said lower portion 162 is positioned in the recess 108,128 of the base member, the transverse holes 114,134 of the base member and the lower portion 162 of the post member 160 are co-linear. The post member 160 is securely retainable in the recess 108,128 of the base member by means of a locking dowel (see FIGS. 9 and 10) which is insertable into the co-linear transverse hole formed by the above-mentioned transverse holes 114,134 of the base and post 160 members.

The upper portion 166 of the post member 160 includes a widened annular section. The upper surface 168 of this section may be flat or roughened to provide an enhanced frictional dynamic with a metal rod (such as is to be pressed against it—as set forth more fully hereinbelow). The lower surface 170 of the widened annular section defines a cross-section (taken along the axial length of the post member) which is curvate, and preferably has a constant radius of curvature, and most preferably has a radius of curvature equal to the interior curvate surface 152 of the head 140.

Figure 8:
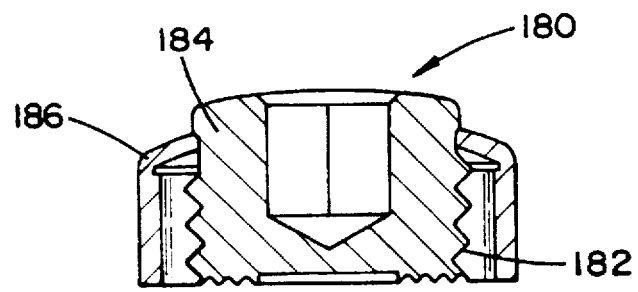
FIG. 8 is a side view of a top locking nut which is an aspect of the present invention.

Referring now to FIG. 8, one possible locking nut 180 is provided in a side cross-section view. The locking nut 180 requires a threading 182 which can mate with and be advanced along the threading 156 of the head portion, so as to lock a rod in the channel 154 (thereinalso providing a downward force onto the top surface of the post 160). This locking nut comprises a central set screw portion 184 and an outer rim portion 186 which seats around the upper portion of the set screw 184 and floats independently until the set screw 184 is fully locked in place on the head 160.

The rod receiving member is a cylindrical element having a central bore and a channel formed transversely therethrough, said channel dividing the upper portion of the member into two upwardly extending curvate elements. The upwardly extending members are preferrably threaded so as to be able to receive a top locking nut of some kind to lock the rod in the channel.

Figure 9:
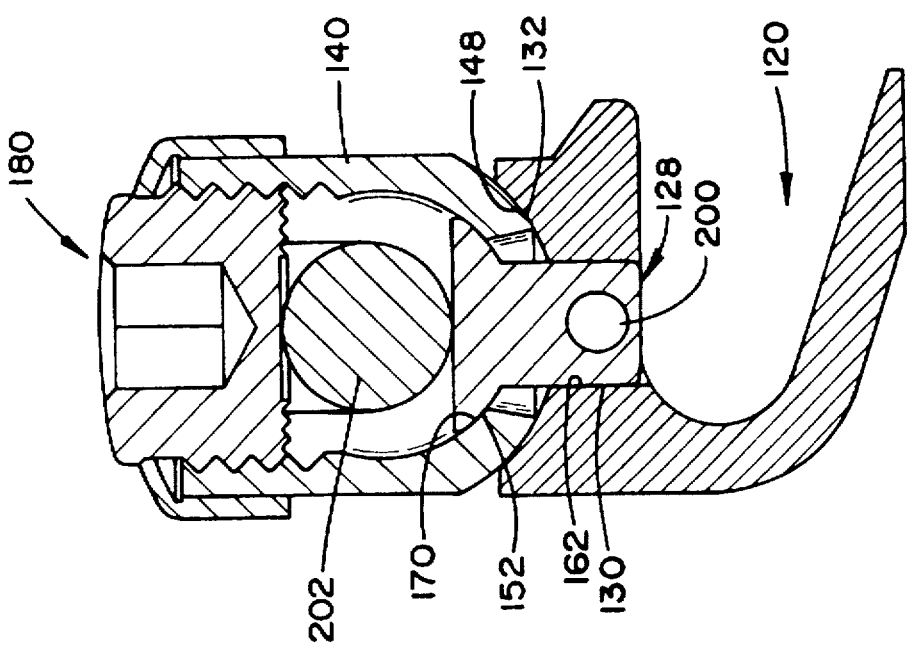
FIG. 9 is a side cross-sectional view of an embodiment of the present invention, a lamina hook embodiment, in its fully assembled disposition in which a dowel is utilized to retain the post member in the base member, and a rod is securely locked therein.
Figure 11:
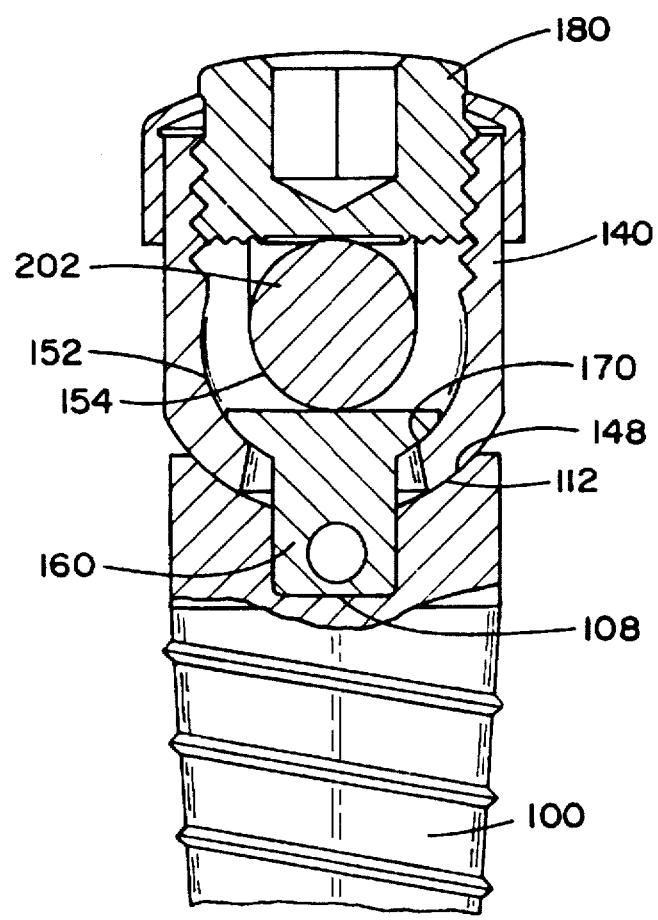
FIG. 11 is a side cross-sectional view of an embodiment of the present invention, a bone screw embodiment, in its fully assembled disposition in which the post member is sweat locked into the recess of the base member.

Referring now to FIGS. 9 and 11), the fully assembled invention is shown in one embodiment, including a hook 120 as the base member. More specifically, with respect to the assembly and function of the invention, in this embodiment, the base member (herein, the hook 120) includes a recess 128 having an upper portion 132 which is curvate. The curvate bottom portion 148 of the head 140 seats in this recess on the curvate surface 132. The post portion 160 is then inserted through the central bore 142 of the head 140 until the lower portion 162 thereof is inserted into the lower portion 130 of the recess 128. The transverse holes in both the post 140 and the base member 120 are aligned and a dowel 200 is placed into the mutually formed hole, thereby preventing the post 160 from being removed from the recess 128 in the base.

In this initial position, the fact that the bottom exterior surface 148 of the head 140 and the upper portion 132 of the recess are substantially concentric, and the diameter of the lower portion of the post 160 is less than that of the bottom of the bore 142, and because of the similar curvature of the lower interior surface 152 of the head and the undersurface 170 of the widened annular top of the post 160, the head can polyaxially spin and rotate on top of the base member and relative to the post 160. The insertion of a rod 202 into the channel 154 of the head 140, and the subsequent advancement of a locking nut 180 onto the head 140 (and thereonto the rod 202) provides a downward force onto the top of the post 160 relative to the head 140. This force, in turn causes the head 140 to rise relative to the post 160 causing the interior surface 152 of the head 140 to crush lock to the undersurface 170 of the post 160.

Referring to FIG. 11, a second embodiment of the present invention is shown in a cross-section view. In particular, this embodiment differs from the one set forth above insofar as it does not require a dowel to hold the post in the recess because the post 160 is "sweat locked" into the recess 128 by means of thermal contraction and expansion, i.e., the post is cooled to a relatively low temperature - therein causing a slight decrease in its diameter as compared with room temperature, and the base member (herein the screw) is raised to a high relative temperature to cause the recess 128 to expand, and subsequently inserting the post into the recess prior to the equilibration of relative temperatures. This "sweat locking" procedure eliminates the need for additional locking means (dowels) and therefore the holes in the post and base.

Insofar as it would be expected that the pre-assembly of the invention, i.e., all but the positioning of the head relative to the base, the insertion of the rod, and the locking of the top nut on the head, would occur prior to the surgeon's manipulation in the operating environment, the two embodiments would be of little difference to the physician.

While there has been described and illustrated embodiments of a polyaxial screw assembly for use with posterior spinal rod implantation apparatus, it will be apparent to those skilled in the art that variations and modifications are possible without deviating from the broad spirit and principle of the present invention. The present invention shall, therefore, be limited solely by the scope of the claims appended hereto.

We claim:

1. A device for stabilizing spinal column segments, comprising:
    a base member which is attachable to a spinal bone said base member having a recess formed in a portion thereof, said recess having a lower portion and an upper portion, said upper portion having a curvate surface;
    a head member having a rod receiving channel and a central bore, said central bore having an inwardly curvate lower interior surface and an inwardly curvate lower exterior surface, said inwardly curvate lower exterior surface being polyaxially seatable on said curvate surface of said recess;
    a post member, having a lower portion which is positionable in said lower portion of said recess in said base member, and a widened annular upper portion which includes a curvate undersurface which seats on the inwardly curvate interior surface of the central bore of the head such that said head is polyaxially rotatable relative to said post, and wherein a top surface of said post remains positioned within the head such that when a rod is positioned in the channel the rod seats on the top surface of the head;
    means for fixedly and rigidly retaining the lower portion of said post in the lower portion of said recess and relative to the base member; and
    a top locking means, engageable with the head member for applying a downward force onto the rod and the post, and a relative upward force on the head such that the curvate undersurface of the widened annular upper portion of the post is crush locked to the inwardly curvate lower interior surface of the central bore of the head.

2. The device as set forth in claim 1, wherein the base member and the post member each further include through holes formed in the lower portions thereof, said through holes being transverse to the long axes of each, and being alignable when the lower portion of the post is inserted into the recess, and further wherein said means for retaining said post in said recess comprises a dowel which is insertable through said through holes when they are aligned.

3. The device as set forth in claim 1, wherein the diameter of said lower portion of said post member is greater than the diameter of the lower portion of the recess when said post member and said base member are at equal temperatures, but wherein said diameter of said post is smaller than the diameter of the lower portion of the recess when the post is held at a temperature which is less than the temperature of the base, and wherein the means for retaining said post in said recess comprises sweat locking said lower portion of said post into said lower portion of said recess.

4. The device as set forth in claim 1, wherein the base member is a lamina hook.

5. The device as set forth in claim 1, wherein the base member is a pedicle screw.

6. A device for stabilizing spinal column segments, comprising:
    at least one rod;
    a plurality of implant devices for coupling a rod to a bone, at least one of said devices including
        a base member which is attachable to a spinal bone said base member having a recess formed in a portion thereof, said recess having a lower portion and an upper portion, said upper portion having a curvate surface,
        a head member having a rod receiving channel and a central bore, said central bore having an inwardly curvate lower interior surface and an inwardly curvate lower exterior surface, said inwardly curvate lower exterior surface being polyaxially seatable on said curvate surface of said recess,
        a post member, having a lower portion which is positionable in said lower portion of said recess in said base member, and a widened annular upper portion which includes a curvate undersurface which seats on the inwardly curvate interior surface of the central bore of the head such that said head is polyaxially rotatable relative to said post, and wherein a top surface of said post remains positioned within the head such that when a rod is positioned in the channel the rod seats on the top surface of the head,
        means for fixedly and rigidly retaining the lower portion of said post in the lower portion of said recess and relative to the base member, and
        a top locking means, engageable with the head member for applying a downward force onto the rod and the post, and a relative upward force on the head such that the curvate undersurface of the widened annular upper portion of the post is crush locked to the inwardly curvate lower interior surface of the central bore of the head.

7. The device as set forth in claim 6, wherein the base member and the post member each further include through holes formed in the lower portions thereof, said through holes being transverse to the long axes of each, and being alignable when the lower portion of the post is inserted into the recess, and further wherein said means for retaining said post in said recess comprises a dowel which is insertable through said through holes when they are aligned.

8. The device as set forth in claim 6, wherein the diameter of said lower portion of said post member is greater than the diameter of the lower portion of the recess when said post member and said base member are at equal temperatures, but wherein said diameter of said post is smaller than the diameter of the lower portion of the recess when the post is held at a temperature which is less than the temperature of the base, and wherein the means for retaining said post in said recess comprises sweat locking said lower portion of said post into said lower portion of said recess.

9. The device as set forth in claim 6, wherein the base member is a lamina hook.

10. The device as set forth in claim 6, wherein the base member is a pedicle screw.

* * * * *